United States Patent [19]
Pommer et al.

[11] 3,954,993
[45] May 4, 1976

[54] FUNGICIDAL COMPOSITION AND PROCESS

[75] Inventors: Ernst-Heinrich Pommer, Limburgerhof; Rudolf Polster, Frankenthal; Friedrich Loecher, Limburgerhof, all of Germany

[73] Assignee: BASF Aktiengesellschaft, Ludwigshafen (Rhine), Germany

[22] Filed: July 30, 1974

[21] Appl. No.: 493,099

[30] Foreign Application Priority Data
Aug. 11, 1973 Germany............................ 2340741

[52] U.S. Cl................................. 424/300; 424/273; 424/309
[51] Int. Cl.² ....................... A01N 9/02; A01N 9/12; A01N 9/20; A01N 9/22
[58] Field of Search............................ 424/300, 309

[56] References Cited
UNITED STATES PATENTS
3,745,187    7/1973    Noguchi et al. ................ 260/455 A FOREIGN PATENTS OR APPLICATIONS
1,218,792    6/1966    Germany

*Primary Examiner*—Sam Rosen
*Assistant Examiner*—Allen J. Robinson
*Attorney, Agent, or Firm*—Johnston, Keil, Thompson & Shurtleff

[57] ABSTRACT

A fungicidal composition comprising different active ingredients, and a process for controlling fungi with this composition. The essential ingredients are (a) diisopropyl 3-nitroisophthalate and (b) a compound selected from the group consisting of thiophanate, thiophanate M, carbendazim and benomyl, and when used in the prescribed combination are useful in preventing fungus growth caused by powdery mildews.

7 Claims, No Drawings

FUNGICIDAL COMPOSITION AND PROCESS

The present invention relates to a fungicide containing a mixture of different active ingredients.

It is known to use diisopropyl 3-nitroisophthalate (German Patent 1,218,792) and benzimidazole and benzene derivatives (Dutch Laid-Open Application 6,706,331, Belgian Patent 698,073 and German Laid-Open Application 1,806,123) as fungicides.

We have now found that a composition of
a. diisopropyl 3-nitroisophthalate and
b. a fungicide selected from the group consisting of
  1,2-bis-(3-ethoxycarbonyl-2-thioureido)-benzene (thiophanate)
  1,2-bis(3-methoxycarbonyl-2-thioureido)-benzene (thiophanate M)
  methyl 2-benzimidazolecarbamate (carbendazim)
  methyl 1-(butylcarbamoyl)-2-benzimidazolecarbamate (benomyl)

has a much better fungicidal action than its components.

The fungicides of the invention are in particular suitable for the curative control of plant diseases caused by powdery mildews such as Erysiphe cichoriacearum in cucurbitaceae, Erysiphe graminis in wheat, Sphaerotheca pannosa in roses, Uncinula necator in grapes, and Podosphaera leucotricha in apples.

The ratio of the active ingredients to each other may vary within wide limits; it is however preferred to use a ratio of a:b of from 1:1 to 4:1, particularly 2:1.

When the compositions of the invention are used for treating plants, application rates vary from 0.5 to 6 kg per hectare.

Application may be effected for instance in the form of directly sprayable solutions, powders, suspensions, dispersions, emulsions, oil dispersions, pastes and dusts. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils and oils of vegetable or mineral origin, aliphatic, cyclic and aromatic hydrocarbons such as benzene, toluene, xylene, paraffin, tetrahydronaphthalene, alkylated naphthalenes, methanol, ethanol, propanol, butanol, chloroform, carbon tetrachloride, cyclohexanol, cyclohexanone, chlorobenzene, isophorone, etc., and strongly polar solvents such as dimethylformamide and dimethyl sulfoxide are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers.

Examples of solid carriers are mineral earths such as silica gel, silicic acid, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

There may be added to the compositions or individual active ingredients oils of various types, fungicides, nematocides, insecticides, bactericides, trace elements, fertilizers, antifoams (e.g., silicones), growth regulators, antidotes and other compounds.

One or more substances from the same of different groups may be added in a ratio by weight of from 1:10 to 10:1.

EXAMPLE 1

Fully developed leaves of cucumber plants kept in a greenhouse at a temperature of from 22° to 25°C and a relative humidity of from 60° to 70°C are artificially infected by dusting them with conidia of the fungus Erysiphe cichoriacearum (cucumber powdery mildew). After an incubation period of 8 to 10 days small almost circular fungus mycelium colonies having a diameter of 3 to 8 and more millimeters become plainly visible on the upper surfaces of the leaves. At this point the leaves are treated by spraying them with aqueous suspensions of compositions of the active ingredients in the mixture and weight ratios given in the table; the individual components are used as comparative agents. Six days after spraying the action of the agents is assessed in accordance with the following scale:

0 = no curative action (control)
1 = fungus growth checked (prophylactic action)
2 = at least 50% of fungus destroyed
3 = fungus completely destroyed

| Active ingredient | Ratio | Amount of active ingredient in liquor in % | Action |
|---|---|---|---|
| diisopropyl 3-nitroisophthalate | — | 0.05 | 0 |
|  | — | 0.1 | 1 |
|  | — | 0.2 | 1 |
| thiophanate | — | 0.025 | 1 |
|  | — | 0.05 | 1 |

-continued

| Active ingredient | Ratio | Amount of active ingredient in liquor in % | Action |
|---|---|---|---|
| | — | 0.075 | 1 |
| thiophanate M | — | 0.025 | 1 |
| | — | 0.05 | 1 |
| | — | 0.075 | 1 |
| carbendazim | — | 0.025 | 0 |
| | — | 0.05 | 0 |
| | — | 0.075 | 0 |
| benomyl | — | 0.025 | 0 |
| | — | 0.05 | 0 |
| | — | 0.075 | 0 |
| diisopropyl 3-nitro-isophthalate + thiophanate | 1:1 | 0.05 + 0.05 | 3 |
| | 2:1 | 0.1 + 0.05 | 3 |
| | 4:1 | 0.1 + 0.025 | 3 |
| + thiophanate M | 1:1 | 0.05 + 0.05 | 3 |
| | 2:1 | 0.05 + 0.025 | 3 |
| | 4:1 | 0.1 + 0.025 | 3 |
| +carbendazim | 2:1 | 0.1 + 0.05 | 3 |
| | 4:1 | 0.1 + 0.025 | 2 |
| + benomyl | 1:1 | 0.05 + 0.05 | 2 |
| | 2:1 | 0.1 + 0.05 | 3 |
| control (untreated) | — | — | 0 |

EXAMPLE 2

Fully developed leaves of potted vines of the "Muller-Thurgau" variety are, as described in Example 1, artificially infected with conidia of the fungus Uncinula necator (grape powdery mildew). After an incubation period of 12 to 14 days small almost circular fungus mycelium colonies having a diameter of several millimeters become clearly visible on the upper surfaces of the leaves. At this point the leaves are treated, and the results assessed, in the same manner as described in Example 1.

| Active ingredient | Ratio | Amount of active ingredient in spray liquor in % | Action |
|---|---|---|---|
| diisopropyl 3-nitro-isophthalate | — | 0.05 | 0 |
| | — | 0.1 | 1 |
| | — | 0.2 | 1 |
| thiophanate M | — | 0.025 | 1 |
| | — | 0.05 | 1 |
| | — | 0.075 | 1 |
| carbendazim | — | 0.025 | 1 |
| | — | 0.05 | 1 |
| | — | 0.075 | 1 |
| diisopropyl 3-nitro-isophthalate + thiophanate M | 2:1 | 0.05 + 0.025 | 3 |
| + carbendazim | 2:1 | 0.05 + 0.025 | 3 |
| control (untreated) | — | — | 0 |

EXAMPLE 3

Fully developed leaves of apple seedlings are, as described in Example 1, artificially infected with conidia of the fungus Podosphaera leucotricha (apple powdery mildew). After an incubation period of 8 to 10 days small almost circular fungus mycelium colonies having a diameter of 3 to 6 millimeters become clearly visible on the upper surfaces of the leaves. At this point the leaves are treated, and the results assessed, in the same manner as described in Example 1.

| Active ingredient | Ratio | Amount of active ingredient in spray liquor in % | Action |
|---|---|---|---|
| diisopropyl 3-nitro-isophthalate | — | 0.05 | 0 |
| | — | 0.1 | 0 |
| | — | 0.2 | 1 |
| thiophanate M | — | 0.025 | 1 |
| | — | 0.05 | 1 |
| | — | 0.075 | 2 |
| carbendazim | — | 0.025 | 1 |
| | — | 0.05 | 1 |
| | — | 0.075 | 1 |
| diisopropyl 3-nitro-isophthalate + thiophanate M | 1:1 | 0.025 + 0.025 | 3 |
| | 2:1 | 0.05 + 0.025 | 3 |
| + carbendazim | 1:1 | 0.025 + 0.025 | 3 |
| | 2:1 | 0.05 + 0.025 | 3 |
| control (untreated) | — | — | 0 |

We claim:

1. A fungicidal composition for controlling the growth of powdery mildew fungi, said composition comprising a mixture of:
   a. diisopropyl 3-nitroisophthalate; and
   b. a compound selected from the group consisting of 1,2-bis-(3-ethoxycarbonyl-2-thioureido)-benzene and 1,2-bis-(3-methoxycarbonyl-2-thioureido)-benzene, the weight ratio of a:b being from 1:1 to 4:1.

2. The fungicidal composition of claim 1 wherein component (b) is 1,2-bis-(3-ethoxycarbonyl-2-thioureido)-benzene.

3. The fungicidal composition of claim 1 wherein component (b) is 1,2-bis-(3-methoxycarbonyl-2-thioureido)-benzene.

4. The fungicidal composition of claim 1 wherein the weight ratio of a:b is approximately 2:1.

5. A process for controlling the growth of powdery mildew fungi which comprises applying to the area infected with said powdery mildew fungi as the active fungicidal composition a mixture of
   a. diisopropyl 3-nitroisophthalate and
   b. a compound selected from the group consisting of 1,2-bis-(3-ethoxycarbonyl-2-thioureido)-benzene and 1,2-bis-(3-methoxycarbonyl-2-thioureido)-benzene, the weight ratio of a:b being from 1:1 to 4:1, said composition being applied in an amount toxic to said powdery mildew fungi.

6. The process of claim 5 wherein the active fungicidal composition is applied to a cultivated plant infected with said powdery mildew fungi.

7. The process of claim 6 wherein the active fungicidal composition is applied to said cultivated plant at a rate of 0.5 to 6 kg per hectare.

* * * * *